United States Patent [19]

Hardtmann

[11] 4,187,309
[45] Feb. 5, 1980

[54] 4-HYDROXY-2-QUINOLINONE-3-CARBOXYLIC ACIDS AND SALTS THEREOF

[75] Inventor: Goetz E. Hardtmann, Morristown, N.J.

[73] Assignee: Sandoz, Inc., East Hanover, N.J.

[21] Appl. No.: 807,914

[22] Filed: Jun. 20, 1977

[51] Int. Cl.$^2$ ............................................. A61K 31/47
[52] U.S. Cl. ..................................... 424/258; 546/155
[58] Field of Search ................... 260/287 K, 287 AN; 424/258

[56] References Cited

U.S. PATENT DOCUMENTS

| | | | |
|---|---|---|---|
| 3,772,305 | 11/1973 | Hellerbach | 260/287 K |
| 3,960,868 | 6/1976 | Ferrini et al. | 260/287 AN |
| 4,107,310 | 8/1978 | Allais et al. | 424/258 |
| 4,119,720 | 10/1978 | Hardtmann | 424/258 |

FOREIGN PATENT DOCUMENTS

| | | | |
|---|---|---|---|
| 806848 | 10/1973 | Belgium . | |
| 2421121 | 1/1975 | Fed. Rep. of Germany . | |
| 2705446 | 8/1977 | Fed. Rep. of Germany . | |
| 814843 | 5/1973 | France . | |
| 44-24596 | 10/1969 | Japan | 260/287 K |
| 7406271 | 9/1975 | South Africa . | |
| 1121411 | 1/1967 | United Kingdom | 260/287 K |
| 1504709 | 3/1978 | United Kingdom . | |

OTHER PUBLICATIONS

Brown, "Australian J. Chem.", (1954), vol. 8, pp. 348–377.
McCorkindale, Tetrahedron, (1961), vol. 14, pp. 223–229.
Brown, Aust. J. of Chem., vol. 8, 1955, pp. 121–124.
Asahina et al., Berich. Deutschen Chem. Gesellschaft, vol. 63, 1930, p 2052ff.
Grundon et al., Source not available, (1955), pp. 4284–4290.
Mitscher et al., Heterocycles, vol. 3, No. 11, (1975), pp. 913—919.
Coutts et al., J. Chem. Soc., (1962), 2518–2521 C.A. vol. 57:5891(b) provided.

*Primary Examiner*—David Wheeler
*Attorney, Agent, or Firm*—Gerald D. Sharkin; Richard E. Vila

[57] ABSTRACT

Disclosed are compounds which are 4-hydroxy-2-quinolinone-3-carboxylic acids and salts thereof, e.g., 1-allyl-6,7-dimethoxy-4-hydroxy-2-quinolinone-3-carboxylic acid, useful as anti-allergic agents, and prepared by hydrolysis of the corresponding carboxylic acid esters.

64 Claims, No Drawings

4-HYDROXY-2-QUINOLINONE-3-CARBOXYLIC ACIDS AND SALTS THEREOF

DISCLOSURE OF THE INVENTION

The present invention relates to chemical compounds and their use as pharmaceutical agents, and more particularly to compounds which are 4-hydroxy-2-quinolinone-3-carboxylic acids and salts which are useful as anti-allergic agents.

The compounds of the present invention consists of the free acids represented by the structural formula I:

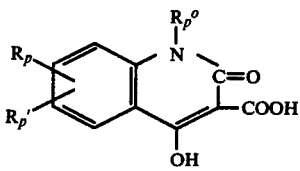

wherein $R_p{}^o$—is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 to 2 carbon atoms, or

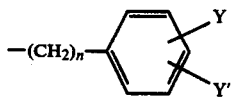

n—is 0 or 1,

Y and Y'—are independently hydrogen, halo of atomic weight of from 18 to 80, i.e., fluoro, chloro or bromo, alkyl of 1 to 3 carbon atoms, alkoxy of 1 to 3 carbon atoms, trifluoromethyl or nitro, with the proviso that only one of Y and Y' can be from the group consisting of nirro and trifluoromethyl, and $R_p$ and $R_p'$—are independently hydrogen, halo of atomic weight of from 18 to 80, i.e., fluoro, chloro or bromo, alkyl of 1 to 4 carbon atoms, alkoxy of 1 to 4 carbon atoms, nitro or trifluoromethyl, or $R_p$ and $R_p'$ together form 6,7-methylenedioxy, with the proviso that only one of $R_p$ and $R_p'$ can be from the group consisting of nitro and trifluoromethyl, with the further proviso that the unsaturation in any alkenyl or alkynyl is on other than the alpha carbon atom; and the monosalt and disalt forms thereof in which the salt-forming cation is a pharamceutically acceptable cation.

The compounds of the formula I in disalt form may be prepared by treating the corresponding carboxylic acid ester of the formula II:

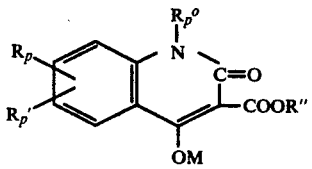

wherein $R_p{}^o$, $R_p$ and $R_p'$ are as above defined, M is hydrogen or a pharmaceutically acceptable cation and R" is alkyl of 1 to 6 carbon atoms, eg. ethyl, with a saponifying base, eg. sodium hydroxide, in an aqueous medium, eg. water or aqueous ethanol, at moderate temperatures of from 40° C. to 150° C., preferably 80° C. to 120° C., followed by recovery in a conventional manner that avoids acidification that can lead to undesired decarboxylation. When M is hydrogen in Compound II it will be evident that at least 2 mols of base are used and in general 2 or more mols are preferably employed. Hence, it will be evident that this reaction will also affect the 4-position substitutent and introduce the cation of the base at the 4-position when M in the starting compound II is hydrogen or produce other disalt forms of the compounds I in which the cations are the same or different when M in the starting compound is itself a cation, depending largely on known factors such as the strong base and the amount thereof that is used. A wide variety of bases may be employed as will be evident, including alkali metal hydroxide, alkaline earth metal hydroxides and ammonium and tetraalkylammonium hydroxides. However, the base is preferably an alkali metal hydroxide an M hydrogen in the compound II, such that the cations in the disalt product of the formula I are the same alkali metal, preferaby sodium or potassium.

The compounds of the formula I in free acid form may be produced by subjecting a compound of the formula II in which R" is a highly acid-labile alkyl group, desirably t-butyl, to mild temperature but otherwise conventional acid catalysed decomposition. In such reaction the temperature conditions are controlled, eg. from minus 20° C. to plus 60° C., preferably from minus 10° C. to 35° C., in order to avoid decarboxylation of the compound I. Acids of known conventional types for such acid decompositions may be employed. Representative such acids include sulfuric acid, hydrochloric acid, and perchloric acid, preferably the latter. The decomposition is suitably carried out in conventional solvent systems for such decompositions, such as a water miscible non-hydroxylic organic solvent such as acetonitrile, tetrahydrofuran and the like, preferably acetonitrile, such solvent systems preferably containing only small amounts of water.

The compounds of the formula I in free acid or monosalt form may also be treated with essentially any desired base, preferably an alkali metal hydroxide such as sodium hydroxide or potassium hydroxide, in an appropriate solvent such as water or aqueous ethanol and over a wide temperature range up to at least about 150° C., preferably 0° C. to 60° C., to obtain, depending upon known factors such as the significance of M in the starting material and the amount of base, the compounds I in monosalt or disalt form. Hence, the treatment of the compound I in free acid form with one mol of base yields the monosalt form in which, because of the tautomerism between the adjacent acidic (4-hydroxy and 3-carboxyl) functions, the salt forming cation is ionically associated with both said 3- and 4-position functions in the known manner of essentially forming an additional six membered ring that includes the cation.

The compounds of the formula II are also similarly useful as anti-allergic agents and are described in copending but soon to be abandoned application Ser. No. 662,148 (filed Feb. 27, 1976) and a continuation-in-part application cofiled with the instant application as Ser. No. 807,898. Such compounds II may be conveniently prepared by reacting a compound of the formula III:

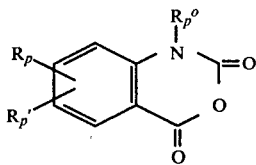

in which $R_p^o$, and $R_p$ and $R_p'$ are as defined above, with a compound of formula IV:

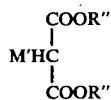

in which
R" is as defined above, and
M' signifies an alkali metal.

The process is suitably carried out in an inert organic solvent, e.g., dimethylacetamide, and at a temperature of from 0° C. to 150° C., preferably 60° C. to 120° C. followed, if necessary or desired, by neutral or acid hydrolysis to obtain the desired compound II from any 4-alkali metal salt thereof initially produced.

The compounds of formula IV may be produced from the corresponding dialkyl malonates by reaction with a strong alkali metal base, e.g., sodium hydride, and in an inert organic solvent, e.g., dimethylacetamide.

The compounds II in wich M is a pharmaceutically acceptable cation, e.g., lithium, sodium, potassium, ammonium, etc., may be also prepared from the compound II in which M is hydrogen by procedures well known in the art, e.g., by treating with a base such as dilute aqueous sodium hydroxide in a water miscible solvent.

The resulting compounds of formula II may be isolated and purified using conventinal techniques.

The compounds of the formula III and IV employed in the preparation of compound II are either known or may be produced in conventional manner from known materials, or as described herein.

The compound 1-methyl-4-hydroxy-2-quinolinone-3-carboxylic acid is known from Mitscher et al., Heterocycles, Vol. 3, No. 11, pages 913-919 (1975), but to my knowledge has not been associated with any useful pharmacological activity. Accordingly, most of the compounds of the formula I are novel and novel subgroupings within the scope of compounds I of particular interest as anti-allergic agents include those in which $R_p$ and $R_p'$ are other than 6,7-methylenedioxy and $R_p^o$ is: (a) alkenyl of 3 to 6 carbon atoms; (b) alkynyl of 3 to 6 carbon atoms; (c) cycloalkyl of 3 to 6 carbon atoms; (d) cycloalkylalkyl in which the cycloalkyl portion is of 3 to 6 carbon atoms and the alkyl portion is 1 to 2 carbon atoms; (e) Y,Y'-substituted phenyl wherein Y and Y' are as above defined: and (f) Y,Y'-substituted benzyl wherein Y and Y' are as above defined. Also of particular interest are the compounds of the formula I in which $R_p^o$ is hydrogen, $R_p$ is hydrogen, fluoro, chloro, bromo, alkyl of 1 to 4 carbon atoms or alkoxy of 1 to 4 carbon atoms and $R_p'$ is fluoro, chloro, bromo, alkyl of 1 to 4 carbon atoms or alkoxy of 1 to 4 carbon atoms. Similarly of particular interest are the compounds I in which $R_p^o$ is alkyl and $R_p$ and $R_p'$ are independently hydrogen, fluoro, chloro, bromo, alkyl of 1 to 4 carbon atoms or alkoxy of 1 to 4 carbon atoms.

Generally preferred compounds I ($R_p$ and $R_p'$ being other than methylenedioxy) are those having one or more, preferably all three, of the following features: (a) $R_p^o$ being hydrogen, alkyl or alkenyl, more preferably alkyl or alkenyl, most preferably allyl; (b) $R_p$ and $R_p'$ both being alkoxy, more preferably representing 6,7-dialkoxy, most preferably 6,7-dimethoxy; and (c) the compounds in free acid or disalt form, more preferably free acid form. Accordingly, representative additional novel subgrouping provided by the invention include those in which $R_p^o$ is alkyl or alkenyl, particularly allyl, and $R_p$ and $R_p'$ represent dialkoxy, more preferably 6,7-dialkoxy, and more preferably 6,7-dimethoxy.

A further novel subgrouping provided by this invention are those compounds I in which $R_p$ and $R_p'$ together form 6,7-methylenedioxy, and the preferred significances of $R_p^o$ in such compounds are alkyl and alkenyl, more preferably allyl; such compounds preferably being in free acid or disalt form, more preferably free acid form.

The compounds of formula I (in free acid or mono- or disalt form) are useful because they possess pharmacological activity in animals. In particular they possess disodium chromoglycate (DSCG)-like activity, in particular histamine release inhibiting activity, and are therefore useful in the treatment of allergic conditions, such as allergic asthma, as indicated in the passive cutaneous anaphylaxis test in the rat. Female rats (180-200 g) are sensitised by subcutaneous administration of 1 mg of egg albumin (Merck Nr.967) and 200 mg. of $Al(OH)_3$ dissolved in 1 ml of physiological saline and 0.5 ml of Haemophiluspertussis vaccine (Schweizerisches Serum and Impfinstitut, Bern; Nr. 115 325; $4 \times 10^{10}$ organism/ml) intraperitoneally. Fourteen days later, the animals are exsanguinated, the blood centrifuged, the serum collected and deep frozen. The serum thus obtained (anti-serum) is injected intradermally (Q.1 ml of a 1:200 diluted serum per injection site) at four sites on the backs of untreated, female rats. Twenty-four hours later each rat is administered 0.1 to 5.6 mg/kg i.v. or 0.1 1 to 100 mg/kg p.o. of the test compound, and either immediately or 5 to 30 minutes afterwards, in the case of intravenous administration, or 15 or 60 minutes afterwards, in the case of oral administration, afterwards egg albumin (5 mg/ml i.v.) dissolved in physiological saline containing 0.25% Evans Blue dye (Merck Nr. 3169). The egg albumin elicits a cutaneous anaphylactic reaction, the intensity of which is proportional to the extent to which the Evans Blue dye diffuses into the tissue surrounding each of the four sensitisation sites. Thirty minutes after the administration of the egg albumin, the rats are killed with ether, the underside of the skin of the back of each animal is exposed and the diameter of the areas of blue dye surrounding each of the four sensitisation sites are measured. Each dose of test compound is investigated in between four and six rats and the mean diameter compared with the mean value obtained in four solvent-treated control rats. The percentage inhibition is taken as the percentage of the mean diameter in the test animals relative to the mean diameter in the controls.

The DSCG-like activity, in particular histamine release inhibiting activity, can be confirmed by inhibition of histamine release in the rat peritoneal mast cell test, basically as described by Kusner et al., J. Pharmacol. Exp. Therap. 184, 41-46 (1973), with the following modification: after sedimentation of the mast cells by centrifugation at $350 \times g$ and 4° C., the sediments are taken up in 1 ml of Hank's balanced salt solution (HBSS) (buffered to a pH of 6.9) and pooled. The resulting suspension is centrifuged, washed again with HBSS and sedimented. The thus purified mast cells are prepared as 2 ml suspensions in HBSS. To these are added either 2 ml of HBSS, to determine the spontaneous histamine release, or 2 ml of HBSS and 2.24 µg of compound 48/80 (N-methylhomoanisylamineformaldehyde condensate; a histamine liberator from Burroughs Wellcome and Co. Inc., Tuckahoe, N.Y. USA), to determine the 48/80 induced histamine release, or 2 ml of HBSS with 2.24 µg of 48/80 and from 18 to 180 µg/ml of the test compound, to determine the 48/80 induced histamine release in the presence of the test compound.

The 48/80 induced histamine release minus the spontaneous histamine release is taken as 100% histamine release. The 48/80 induced histamine release in the presence of the test compound minus the spontaneous histamine release is then compared with the 100% value to determine the percentage inhibition by the test compound. [The histamine determination is effected in conventional manner, for example, as described in the above-mentioned Kuzner et al. article, or in Kusner and Herzig, Advances in Automated Analysis, 429 (1971)].

For the above-mentioned anti-allergic use, the dosage administered will, of course, vary depending on the compound employed, mode of administration and treatment desired. However, satisfactory results are generally obtained on the administration of compounds I at a daily dosage of from about 0.1 to 100 mg/kg of animal body weight, conveniently given in divided doses two to four times daily, or in sustained release form. For the larger mammals, the total daily dosage is in the range of from about 20 to 800 mg of the compound admixed with a solid or liquid pharmaceutical carrier, of conventional type, and divided dosage forms comprise 5 to 400 milligrams of the compound in admixture with a solid or liquid pharmaceutical carrier. As will be appreciated, the treatment of allergic conditions according to the invention is based on histamine release inhibition activity and is therefore essentially symptomatic. The ability to employ such compounds in prophylactic treatment of such allergic conditions (as evident from the DSCG-like activity) is a feature of such compounds. However, the good oral activity relative to DSCG is a further feature.

Pharmaceutical compositions provided by the invention and useful for treating allergic conditions due to histamine release contain a compound of the formula I as active ingredient and one or more conventional pharmaceutically acceptable carriers, and such other conventional adjuvants as may be desired or necessary. Such compositions may be in conventional orally administerable forms such as tablets, capsules, granules, dispersible powders, elixirs, syrups, suspensions and the like or in conventional parenterally administerable forms such as an injectable sterile solution, suspension or the like, e.g., a sterile injectable aqueous suspension. Such compositons including applicable unit dosage forms thereof may be prepared according to any method known in the art for the manufacture of pharmaceutical compositions. The compounds may also be administered by inhalation therapy techniques in compositions conventionally prepared and adapted for such procedures. The compositions of the invention adapted for either oral, inhalation or parenteral administration may contain from 1% to 90% by total weight of active ingredient in combination with the carrier, more usually 3% to 70%. The preferred unit dosage forms are the essentially solid forms adapted for oral administation, e.g., tablets or capsules.

A representative formulation for administration 2 to 4 times a day for prophylactic treatment of allergic asthma is a capsule prepared by standard techniques to contain the following:

| Ingredient | Weight (mg) |
|---|---|
| 1-Allyl-6,7-dimethoxy-4-hydroxy-2-quinolinone-3-carboxylic acid | 20 |
| Kaolin | 210 |

The following examples are given for purposes of illustration only.

EXAMPLE 1

1-Allyl-6,7-dimethoxy-4-hydroxy-2-quinolinone-3-carboxylic acid

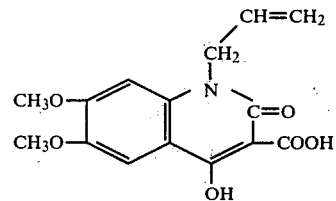

STEP A: Preparation of 1-allyl-6,7-dimethoxy-4-hydroxy-2-quinolinone-3-carboxylic acid t-butyl ester To a solution of 8.3 g. of di-t-butyl malonate in 75 ml. of dimethylacetamide is added portionwise 1.9 g. of pentane washed 50% sodium hydride. The resulting solution is stirred at room temperature for 30 minutes and there is then added 10.0 g. of 1-allyl-6,7-dimethoxyisatoic anhydride in 100 ml. of dimethylacetamide. The resulting solution is heated at 120° C. for 3 hours, the dimethylacetamide removed in vacuo, water added, the resulting mixture washed with methylene chloride, acidified with 2 N. hydrochloric acid and extracted with methylene chloride. The organic phase is dried and evaporated in vacuo to an oil which is crystallized from ether to obtain 1-allyl-6,7-dimethoxy-4-hydroxy-2-quinolinone-3-carboxylic acid t-butyl ester.

STEP B: Preparation of 1-allyl-6,7-dimethoxy-4-hydroxy-2-quinolinone-3-carboxylic acid To a solution of 3.1 g. of 1-allyl-6,7-dimethoxy-4-hydroxy-2-quinolinone-3-carboxylic acid t-butyl ester in 30 ml. of acetonitrile at 0° C. is added 0.75 ml. of 60% aqueous perchloric acid. The resulting precipitate is recovered by filtering and washed with ether to obtain 1-allyl-6,7-dimethoxy-4-hydroxy-2-quinolinone-3-carboxylic acid which melts at 169°–170° C. and decarboxylates at 185°–195° C.

EXAMPLE 2

In manner analogous to Example 1, employing appropriate starting materials in approximately equivalent amounts, the following compounds may be obtained:
(A) 1-hexyl-4-hydroxy-2-quinolinone-3-carboxylic acid.

(B) 1-ethyl-4-hydroxy-2-quinolinone-3-carboxylic acid.
(C) 1-butyl-7-chloro-4-hydroxy-2-quinolinone-3-carboxylic acid.
(D) 1-methyl-6-methoxy-4-hydroxy-2-quinolinone-3-carboxylic acid.
(E0) 1-methyl-6-chloro-4-hydroxy-2-quinolinone-3-carboxylic acid.
(F) 1-methyl-4-hydroxy-2-quinolinone-3-carboxylic acid.
(G) 6-methyl-4-hydroxy-2-quinolinone-3-carboxylic acid.
(H) 1-allyl-4-hydroxy-2-quinolinone-3-carboxylic acid.
(I) 1-(3-butenyl)-6,7-dimethoxy-4-hydroxy-2-quinolinone-3-carboxylic acid.
(J) 6,7-dimethoxy-4-hydroxy-2-quinolinone-3-carboxylic acid.
(K) 6-chloro-4-hydroxy-2-quinolinone-3-carboxylic acid.
(L) 1-cyclopentyl-4-hydroxy-2-quinolinone-3-carboxylic acid.
(M) 1-cyclopropylmethyl-4-hydroxy-2-quinolinone-3-carboxylic acid.
(N) 1-(o-nitrobenzyl)-4-hydroxy-2-quinolinone-3-carboxylic acid.
(O) 1-propargyl-4-hydroxy-2-quinolinone-3-carboxylic acid.
(P) 1-(p-fluorobenzyl)-4-hydroxy-2-quinolinone-3-carboxylic acid.
(Q) 1-phenyl-4-hydroxy-2-quinolinone-3-carboxylic acid.
(R) 1-methyl-6,7-dimethoxy-4-hydroxy-2-quinolinone-3-carboxylic acid ethyl ester, m.p. 216°–219° C.
(S) 1-(2-butynyl)-6,7-dimethoxy-4-hydroxy-2-quinolinone-3-carboxylic acid.
(T) 1-(2-methyl-3-propenyl)-6,7-dimethoxy-4-hydroxy-2-quinolinone-3-carboxylic acid.
(U) 1-propyl-6,7-dimethoxy-4-hydroxy-2-quinolinone-3-carboxylic acid.
(V) 1-cyclopropylmethyl-6,7-dimethoxy-4-hydroxy-2-quinolinone-3-carboxylic acid.
(W) 1-(2-butenyl)-6,7-methoxy-4-hydroxy-2-quinolinone-3-carboxylic acid.
(X) 1-allyl-6,7-methylenedioxy-2-quinolinone-4-hydroxy-3-carboxylic acid.
(Y) 1-allyl-6,7-dichloro-4-hydroxy-2-quinolinone-3-carboxylic acid.
(Z) 1-allyl-6-methoxy-7-ethyl-4-hydroxy-2-quinolinone-3-carboxylic acid.
(Z-1) 1-allyl-6-methoxy-7-methyl-4-hydroxy-2-quinolinone-3-carboxylic acid.
(Z-2) 1-allyl-6,7-dimethyl-4-hydroxy-2-quinolinone-3-carboxylic acid.

Another subgrouping of the compounds I of interest as anti-allergic agents are those in which $R_p^o$ is allyl, $R_p$ is alkyl of 1 to 4 carbon atoms in the 7-position, preferably methyl or ethyl, and $R_p'$ is alkoxy of 1 to 2 carbon atoms in the 6-position, preferably methoxy.

What is claimed is:
1. The method of treating allergic conditions due to histamine release comprising administering to a mammal in need of such treatment an allergy treating effective amount of a compound having in free acid form the formula:

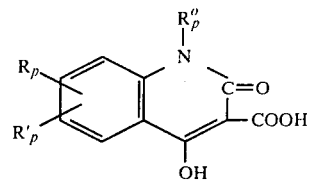

wherein
$R_p^o$ is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 to 2 carbon atoms, or

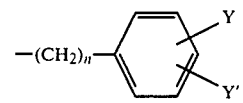

n—is 0 or 1,
Y and Y'—are independently hydrogen, fluoro, chloro, bromo, alkyl of 1 to 3 carbon atoms, alkoxy of 1 to 3 carbon atoms, trifluoromethyl or nitro, with the proviso that only one of Y and Y' can be from the group consisting of nitro and trifluoromethyl, and
$R_p$ and $R_p'$—are independently hydrogen, fluoro, chloro, bromo, alkyl of 1 to 4 carbon atoms, alkoxy of 1 to 4 carbon atoms, nitro or trifluoromethyl, or $R_p$ and $R_p'$ together form 6,7-methylenedioxy, with the proviso that only one of $R_p$ and $R_p'$ can be from the group consisting of nitro and trifluoromethyl, with the further proviso that the unsaturation in any alkenyl or alkynyl is on other than the alpha carbon atom; or a mono- or di-salt form thereof in which the salt forming cation is a pharmaceutically acceptable cation.

2. The method of claim 1 in which $R_p$ and $R_p'$ are independently hydrogen, fluoro, chloro, bromo, alkyl of 1 to 4 carbon atoms, alkoxy of 1 to 4 carbon atoms, nitro or trifluoromethyl.

3. The method of claim 2 in which $R_p^o$ is alkyl.
4. The method of claim 2 in which $R_p^o$ is alkenyl.
5. The method of claim 2 in which $R_p^o$ is hydrogen.
6. The method of claim 2 in which $R_p^o$ is cycloalkyl.
7. The method of claim 2 in which $R_p^o$ is alkynyl.
8. The method of claim 2 in which $R_p^o$ is cycloalkylalkyl.
9. The method of claim 2 in which $R_p^o$ is

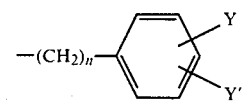

10. The method of claim 9 in which n is 0.
11. The method of claim 9 in which n is 1.
12. The method of claim 1 in which the compound is in free acid form.
13. The method of claim 2 in which $R_p$ and $R_p'$ are each alkoxy.
14. The method of claim 13 in which $R_p$ and $R_p'$ represent 6,7-dialkoxy.

15. The method of claim 14 in which $R_p$ and $R_p'$ represent 6,7-dimethoxy.

16. The method of claim 4 in which $R_p^o$ is allyl.

17. The method of claim 16 in which $R_p$ and $R_p'$ represent 6,7-dimethoxy.

18. The method of claim 3 in which $R_p$ and $R_p'$ represent 6,7-dimethoxy.

19. The method of claim 5 in which $R_p$ is fluoro, chloro, bromo, alkyl of 1 to 4 carbon atoms or alkoxy of 1 to 4 carbon atoms and $R_p'$ is fluoro, chloro, bromo, alkyl of 1 to 4 carbon atoms or akoxy of 1 to 4 carbon atoms.

20. The method of claim 3 in which $R_p$ and $R_p'$ are independently hydrogen, fluoro, chloro, bromo, alkyl of 1 to 4 carbon atoms or alkoxy of 1 to 4 carbon atoms.

21. The method of claim 19 in which the compound is 6,7-dimethoxy-4-hydroxy-2-quinolinone-3-carboxylic acid.

22. The method of claim 20 in which the compound is 1-methyl-4-hydroxy-2-quinolinone-3-carboxylic acid.

23. The method of claim 4 in which the compound is 1-allyl-4-hydroxy-2-quinolinone-3-carboxylic acid.

24. The method of claim 18 in which the compound is 1-allyl-6,7-dimethoxy-4-hydroxy-2-quinolinone-3-carboxylic acid.

25. The method of claim 2 in which the compound is 6-methyl-4-hydroxy-2-quinolinone-3-carboxylic acid.

26. The method of claim 20 in which the compound is 1-methyl-6-chloro-4-hydroxy-2-quinolinone-3-carboxylic acid.

27. The method of claim 11 in which the compound is 1-(p-fluorobenzyl)-4-hydroxy-2-quinolinone-3-carboxylic acid.

28. The method of claim 18 in which the compound is 1-methyl-6,7-dimethoxy-4-hydroxy-2-quinolinone-3-carboxylic acid.

29. The method of claim 1 in which $R_p$ and $R_p'$ together form 6,7-methylenedioxy.

30. The method of claim 20 in which $R_p^o$ is allyl.

31. The method of claim 21 in which the compound is 1-allyl-6,7-methylenedioxy-4-hydroxy-2-quinolinone-3-carboxylic acid ethyl ester.

32. The method of claim 1 in which the compound is administered at a daily dosage of from 40 to 800 milligrams.

33. A pharmaceutical composition comprising in unit dosage form a pharmaceutically acceptable carrier and an amount effective to relieve allergic conditions due to histamine release of a compound having in free acid form the formula:

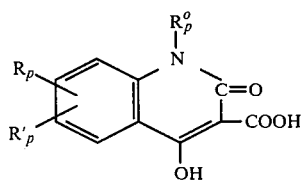

wherein $R_p^o$ is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 to 2 carbon atoms, or

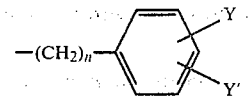

n—is 0 to 1,

Y and Y'—are independently hydrogen, fluoro, chloro, bromo, alkyl of 1 to 3 carbon atoms, alkoxy of 1 to 3 carbon atoms, trifluoromethyl or nitro, with the proviso that only one of Y and Y' can be from the group consisting of nitro and trifluoromethyl, and $R_p$ and $R_p'$—are independently hydrogen, fluoro, chloro, bromo, alkyl of 1 to 4 carbon atoms, alkoxy of 1 to 4 carbon atoms, nitro or trifluoromethyl, or $R_p$ and $R_p'$ together form 6,7-methylenedioxy, with the proviso that only one of $R_p$ and $R_p'$ can be from the group consisting of nitro and trifluoromethyl, with the further proviso that the unsaturation in any alkenyl or alkynyl is on other than the alpha carbon atom; or a mono- or di-salt form thereof in which the salt forming cation is a pharmaceutically acceptable cation.

34. The composition of claim 33 in which $R_p$ and $R_p'$ are independently hydrogen, fluoro, chloro, bromo, alkyl of 1 to 4 carbon atoms, alkoxy of 1 to 4 carbon atoms, nitro or trifluoromethyl.

35. A composition of claim 34 in which $R_p^o$ is alkyl.

36. A composition of claim 34 in which $R_p^o$ is alkenyl.

37. A composition of claim 34 in which $R_p^o$ is hydrogen.

38. A composition of claim 34 in which $R_p^o$ is cycloalkyl.

39. A composition of claim 34 in which $R_p^o$ is alkynyl.

40. A composition of claim 34 in which $R_p^o$ is cycloalkylalkyl.

41. A composition of claim 34 in which $R_p^o$ is

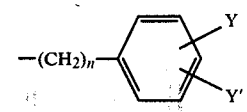

42. A composition of claim 41 in which n is 0.

43. A composition of claim 41 in which n is 1.

44. A composition of claim 33 in which the compound is in free acid form.

45. A composition of claim 33 in which $R_p$ and $R_p'$ are each alkoxy.

46. A composition of claim 45 in which $R_p$ and $R_p'$ represent 6,7-dialkoxy.

47. A composition of claim 46 in which $R_p$ and $R_p'$ represent 6,7-dimethoxy.

48. A composition of claim 36 in which $R_p^o$ is allyl.

49. A composition of claim 48 in which $R_p$ and $R_p'$ represent 6,7-dimethoxy.

50. A composition of claim 35 in which $R_p$ and $R_p'$ represent 6,7-dimethoxy.

51. A composition of claim 37 in which $R_p$ is fluoro, chloro, bromo, alkyl of 1 to 4 carbon atoms or alkoxy of 1 to 4 carbon atoms and $R_p'$ is fluoro, chloro, bromo, alkyl of 1 to 4 carbon atoms or alkoxy of 1 to 4 carbon atoms.

52. A composition of claim 35 in which $R_p$ and $R_p'$ are independently hydrogen, fluoro, chloro, bromo, alkyl of 1 to 4 carbon atoms or alkoxy of 1 to 4 carbon atoms.

53. A composition of claim 51 in which the compound is 6,7-dimethoxy-4-hydroxy-2-quinolinone-3-carboxylic acid.

54. A composition of claim 52 in which the compound is 1-methyl-4-hydroxy-2-quinolinone-3-carboxylic acid.

55. A composition of claim 36 in which the compound is 1-allyl-4-hydroxy-2-quinolinone-3-carboxylic acid.

56. A composition of claim 50 in which the compound is 1-allyl-6,7-dimethoxy-4-hydroxy-2-quinolinone-3-carboxylic acid.

57. A composition of claim 34 in which the compound is 6-methyl-4-hydroxy-2-quinolinone-3-carboxylic acid.

58. A composition of claim 52 in which the compound is 1-methyl-6-chloro-4-hydroxy-2-quinolinone-3-carboxylic acid.

59. A composition of claim 43 in which the compound is 1-(p-fluorobenzyl)-4-hydroxy-2-quinolinone-3-carboxylic acid.

60. A composition of claim 50 in which the compound is 1-methyl-6,7-dimethoxy-4-hydroxy-2-quinolinone-3-carboxylic acid.

61. A composition of claim 33 in which $R_p$ and $R_p'$ together form 6,7-methylenedioxy.

62. A composition of claim 61 in which $R_p^o$ is allyl.

63. A composition of claim 62 in which the compound is 1-allyl-6,7-methylenedioxy-4-hydroxy-2-quinolinone-3-carboxylic acid.

64. A composition of claim 33 containing the compound in an amount of from 10 to 400 milligrams and a solid carrier.

* * * * *